United States Patent [19]

Steele et al.

[11] Patent Number: 5,114,677
[45] Date of Patent: May 19, 1992

[54] GAS DETECTION APPARATUS AND RELATED METHOD

[75] Inventors: Michael F. Steele, Fountain Valley, Calif.; John E. Lambright, South Daytona; George M. Dobson, Deland, both of Fla.

[73] Assignee: Brunswick Corporation, Skokie, Ill.

[21] Appl. No.: 332,129

[22] Filed: Apr. 3, 1989

[51] Int. Cl.$^5$ .................. G01N 27/62; G01N 27/64; G01N 27/66

[52] U.S. Cl. .......................... 422/83; 422/98; 324/464; 324/469

[58] Field of Search ................ 422/83, 98; 324/464, 324/469

[56] References Cited

U.S. PATENT DOCUMENTS 3,601,609  8/1971  Yauger .................. 324/469
4,724,394  2/1988  Langer et al. ............. 422/83

OTHER PUBLICATIONS

Chemical Systems Laboratory Contractor Report ARCSL-CR-81038, "M43E1 Detector Unit Chemical Agent, Automatic", Final Comprehensive Report and Human Factors Engineering Final Report, by Bernard C. Schluter, et al., Honeywell Inc, Jul. 1981, pp. 15–17 M8A1 Chemical Agent Alarm System (2 pages).

*Primary Examiner*—Robert J. Warden
*Assistant Examiner*—Stephanie Blythe
*Attorney, Agent, or Firm*—Finnegan, Henderson, Farabow, Garrett and Dunner

[57] ABSTRACT

The gas detection apparatus for detecting chemical agents in an air stream includes a radioactive source to ionize the air stream and an electrostatic field to increase the efficiency of the apparatus by neutralizing undesired ions, which allows a radioactive source with a lower radiation level to be used than would be required without such neutralization. A diffusion chamber including a baffle device is then used for an ion selection processes. Additional undesired ions are diffused into the walls of the diffusion chamber while the remaining ions, which are the ones sought to be detected, pass from the diffusion chamber into a collection chamber. Detection of the chemical agent ions is achieved when the remaining ions collide with the walls of a collection chamber, transferring their charge to thereby generate a current.

8 Claims, 5 Drawing Sheets

GAS DETECTION APPARATUS AND RELATED METHOD

BACKGROUND OF THE INVENTION

1. Field of the Invention

The present invention relates to gas detectors; and more particularly, to an improved ionization chamber within the gas detection apparatus and corresponding method.

2. The Prior Art

Chemical agent gas detectors are commonly used to sense the presence of various types of toxic gases for activating audio and visual alarms before the arrival of injurious quantities of such gases.

Historically, diffusion chamber gas detection utilizing ion molecule reactions and subsequent detection of the resulting analyte ions by their differing ion mobilities have been accomplished in the following manner. An air sample of constant flow is presented to an irradiation chamber wherein radioactive particles released from a radiation source contained within the chamber initiate the formation by subsequent molecular reaction of reactant ions of the form $(H_2O)_nH^+$ and $(H_2O)_mO_2^-$. These reactant ions generally have values for n and m such that their reduced mobilities are greater than 2.2 $cm^2v^{-1}s^{-1}$. These reactant ions pass from the radiation chamber into a diffusion chamber in which they are acted upon by a complex flow path established by labyrinth geometry and velocity control orifices. These diffusion chamber geometries are configured to generally prevent ions with mobilities of greater than 2.0 $cm^2v^{-1}s^{-1}$ from passing through the chamber by allowing them sufficient resident time exposure within the diffusion chamber to become neutralized either by collision with the large surface area of the tube walls or by recombination with flow stream entrained ions of opposing polarity.

In the case where the air sample presented to the radiation chamber contains a contaminant gas or gas of interest G, a second molecular reaction between the contaminant gas G, and the reactant ions formed in the irradiation chamber occurs. These newly formed molecules are product ions and within their family resides a group of ions of interest which are of the general form $(G)_p(H_2O)_rH^+$ and $(G)_s(H_2O)_tO_2^-$ and which generally have values of p, r, s and t such that their ion mobilities are less than 1.8 $cm^2v^{-1}s^{-1}$. When presented to a diffusion chamber sized for preventing passage of molecules of ion mobilities greater than 2.0 $cm^2v^{-1}s^{-1}$, these low mobility ions remain in the general flow stream thus avoiding neutralization by collision with the diffusion chamber walls. As a result, these group of interest product ions complete passage through the diffusion chamber with charge retention.

Upon exiting the diffusion chamber the flow stream enters a cavity or collection cup. In this cavity the flow velocity is reduced such that neutralization of the product ions of interest is accomplished by collision with the cavity walls and subsequent charge transfer. When a low electrical potential is connected to the cavity or collection cup surface, a small electric current is generated to replace the cup surface electrons lost in the product ion charge transfer process. With suitable electronic amplification and measurement circuitry, this low level electron transfer current can be sensed and, by monitoring its level, the presence of the product ions of interest and thus the contaminant gas or gas of interest G can be detected.

Current devices which utilize this methodology employ either bipolar or monopolar radiation chambers which require high energy and therefore potentially hazardous radiation sources.

In the case of bipolar chambers, this high energy need arises from diffusion and collection chamber flow and velocity requirements that dictate irradiation chamber flow geometries which permit a high percentage of reactant ion recombination losses to occur before the secondary product ion molecular reactions can take place. The resulting loss of sensitivity is currently overcome by increasing the radiation source strength to a level where the initially formed number of reactant ion pairs is sufficiently large enough to allow a detectable number of product ions to be formed prior to completion of the recombination process.

Radioactive particle and subsequent molecular reaction air stream processing within the monopolar irradiation chamber is accomplished by limiting the free travel path of the radiation source emitted radioactive particles. This is accomplished by coating the radiation source with a thin energy absorbing barrier which consumes in the region of 90% of the radioactive emitted particle energy prior to introduction of these particulates into the air stream. Having undergone this energy reduction processing the emitted particulate velocities are reduced to the point where on average they undergo only the final two travel path collisions. At this low collision velocity the radioactive particle which is generally in the form $H^+$ collects and retains the collision freed electrons. This effect leaves a neutralized hydrogen particle and two positively charged nitrogen particles within the ionization chamber for each radioactive particle which permeates the barrier. The collision generated nitrogen particles produce a charge enriched zone but only for a subsequent positive reactant and product ionic reactions and only at the expense of incorporating a radiation source of sufficiently high strength to function in the barrier control mode.

Currently, Americium 241 is used as the high strength radioactive source. However, the use of Americium 241 creates a high potential for radiation hazard to the user of the conventional device.

Although a high strength radioactive source is currently in use, current devices are insensitive to relatively minor quantities of chemical agents in the air.

SUMMARY OF THE INVENTION

It is therefore an object of the present invention to provide an apparatus which will require a relatively small amount of active radiation in order to produce an alarm-level ion transfer current in a cell module used in a chemical agent gas detector.

It is a further object of the present invention to provide an apparatus which has the ability to detect small quantities of chemical agent in an air stream.

Additional objects and advantages of the invention will be set forth in part in the description which follows, and in part will be obvious from the description, or may be learned by practice of the invention. The object and advantages of the invention may be realized and attained by means of the instrumentalities and combinations particularly pointed out in the appended claims.

To achieve the objects and in accordance with the purpose of the invention, as embodied and broadly described herein, a gas detection apparatus is provided and comprises a housing including an ionization chamber, a diffusion chamber, and a collection chamber in communication with each other; means for conducting an air stream through the chambers at a constant rate; radiation means mounted in the ionization chamber for generating reactant and product ions of first and second charge types; means mounted in the ionization chamber for generating an electrostatic field for neutralizing generated ions of the first charge type; baffle means mounted in a diffusion chamber for conducting the ionized air stream through a labyrinthine path for neutralizing reactant ions of the second charge type; and circuit means responsive to the presence of product ions of the second charge type in the collection chamber for completing an electrical circuit.

Thus, the present invention is directed toward an advancement in commercial gas detection wherein the abundance of reactant ions of the charge of interest, formed within a low radiation energy ionization zone of the irradiation chamber, is enhanced based on controlling charged carrier motion and charge neutralizations within the chamber by use of electric field forces.

Theoretically, this technique is based on the phenomenon that electric fields can be used to influence the motion of mobile charge carriers formed by any standard ionization process or subsequent chemical reaction made possible by said ionization process. Further, that said electric field induced motions can be used to sort newly formed mobile charge carrier pairs by charge in a manner which reduces charge concentration losses that occur normally in the recombination collision charge transfer process. More specifically, this invention applies to charge carrier path control for extremely low irradiation energy bipolar ionization chambers wherein an electric field near and within the ionization region segregates the charge carriers formed in the ionization process by polarity.

In this invention, an electric field is formed by applying a voltage potential to a pair of electrodes which bound the ionization, reactant ion formation and product ion formation zones near and about the irradiation chamber. Electric field operation on the carrier gas through the ionization and reactant ion formation processes results in the sorting of the carrier gas ions into positive and negative charge enriched zones. Furthermore, selection of the electric field electrode locations and surface area exposures along the carrier gas flow paths in said ionization and ion formation regions is used to neutralize the charged molecules of said enriched zone having opposing charge polarity to the charge group of interest.

By using controlled electric field forces and flow forces to limit the ion chamber production to ions of a single polarity, the present invention provides a methodology for converting low radiation energy bipolar ionization chambers to monopolar ionization chambers.

The accompanying drawings, which are incorporated in and constitute a part of the specification, illustrate the presently preferred embodiments of the invention and, together with the general description of the invention given above and the detailed description of the preferred embodiments given below, serve to explain the principles of the invention.

DESCRIPTION OF THE PREFERRED EMBODIMENTS

Reference will now be made in detail to the presently preferred embodiments of the invention, examples of which are illustrated in the accompanying drawings in which like reference characters refer to like elements.

The typical chemical agent gas detector may consist of a hand held unit including an ionization cell module for separating ions of interest from an air sample, an amplifier circuit for enhancing detection of ions of interest, and an electronic monitor circuit and alarm circuit which responds to such ion detection. Such a detector may be powered by a low voltage battery, such as an automotive battery, when the unit is mounted on a jeep, or a lighter weight 18 to 36 volt battery when the unit is carried by hand, for example.

Figure 1:
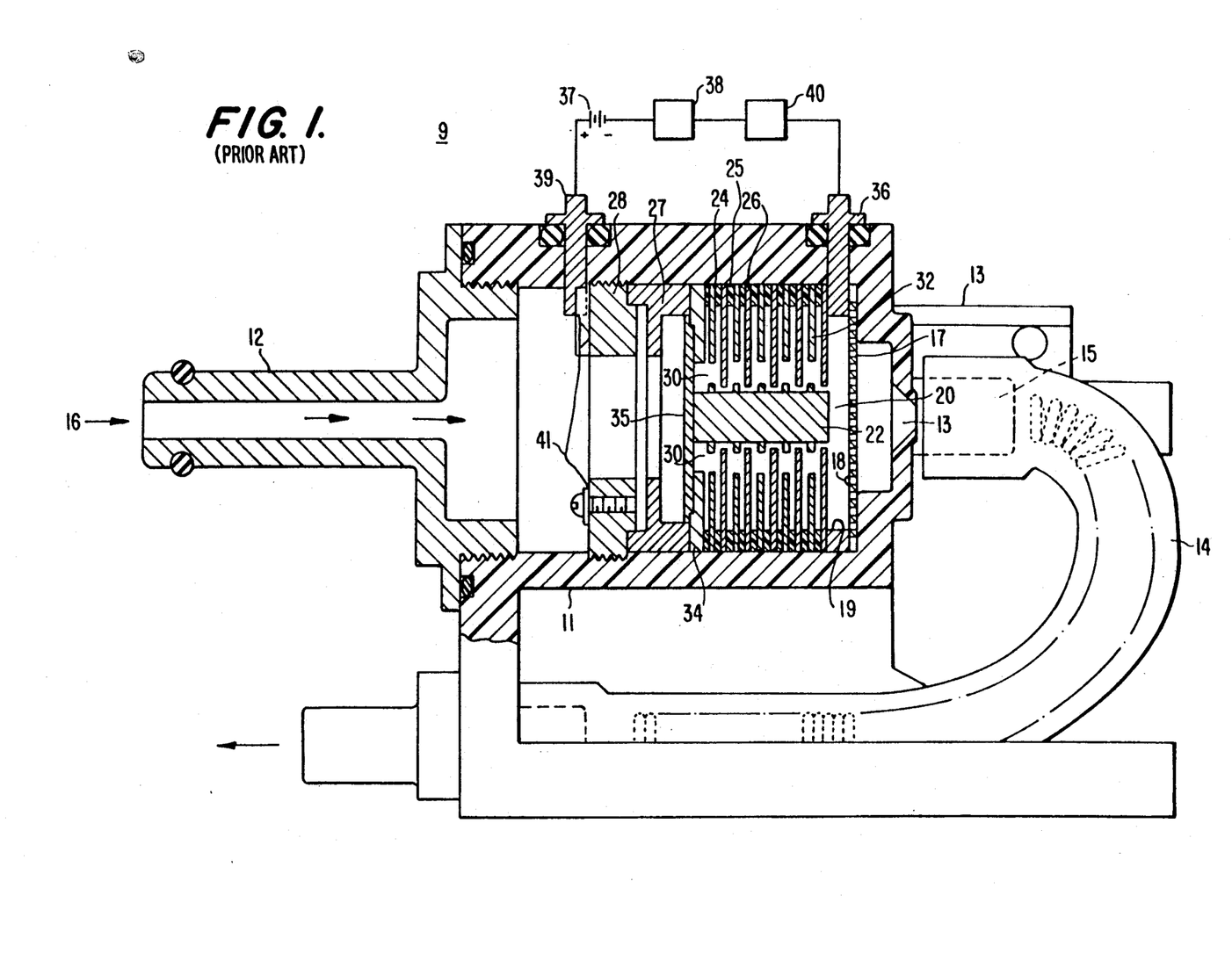
FIG. 1 is a cross-sectional view illustrating a prior art cell module used in a chemical agent gas detection apparatus.

A conventional apparatus of such type, which is used to carry out the ionization detection process, is illustrated in FIG. 1. As shown therein, a gas detector cell module 9 is comprised of a cylindrical, non-conductive housing 11 having portions of reduced internal diameter at opposite ends to form an air stream inlet 12 and an air stream outlet 13. In exhaust piping 14, connected to outlet 13, is an air pump 15 which is mounted to cause an air stream 16 to flow from inlet 12 through housing 11, outlet 13 and exhaust piping 14 at a constant rate. Alternatively, the air pump 15 could be placed downstream of exhaust piping 14 or a blower could be used at inlet 12. In housing 11 adjacent outlet 13, collector grid 17 is mounted to cover outlet 13. Collector grid 17 is retained in position against radial surface 18 in housing 11 by an annular metallic collector ring 19. The chamber formed by collector ring 19 and collector grid 17 may be functionally defined as a collection chamber, referenced by numeral 20.

At the entrance to collection chamber 20 is a baffle assembly comprised of a manifold 22 on which is mounted a coaxial series of circular baffle plates 24. Alternative ones of baffle plates 24 have orifices 30 spaced therein while the other ones 26 of baffle plates 24 have annular openings 25 therein to create a labyrinthine path through the series of spaced baffle plates 24, which labyrinthine path is functionally defined as a diffusion chamber, referred to at 32.

At the entrance to diffusion chamber 32, opposite collector ring 19, is a disk 34 with an annular opening (not shown) therein and having formed on a radial surface thereof, opposing inlet 12, a strong radioactive source 35 with an annular opening therein, which is typically Americium 241. An annular spacer member 27 positions disk 34 against manifold 22. This entire assembly comprised of members 17, 19, 24, 26 and 27 is slidably mounted in housing 11 and retained by annular retainer 28 which is threaded in housing 11 to maintain such members in physical engagement with each other in housing 11.

When air stream 16 is brought into the region which includes radioactive source 35, the radioactive particles released by source 35 undergo reactions with water molecules in the air to form the reactant ions described earlier. In a case where the flow of air entering the radioactive source region contains a chemical agent or a gas of interest G, a second molecular reaction between the gas G and the reactant ions formed in the radioactive source region occurs. These molecules are product ions and within their family is a group of ions of interest of the general form also described earlier. Because the diffusion chamber is designed to prevent passage of molecules with ion mobilities greater than 2.0 $cm^2v^{-1}s^{-1}$, some of the ions will collide with the walls of baffle plates 24 and 26 and will lose their charge, and other ions will lose their charge to ions of opposite polarity by a recombination process and become neutral molecules. The product ions have lower ion mobilities and remain in the general flow stream thus avoiding neutralization by collision with the surface area of the baffles. As a result, a group of product ions of interest complete passage through the baffles retaining their charge.

In collection chamber 20, which is downstream of diffusion chamber 32, the velocity of the air flow is reduced such that neutralization of the product ions is accomplished by collision of product ions with the grid and the inner peripheral surface of collector ring 19 in collection chamber 20, thereby causing the product ions to transfer their charge to grid 17 and collector ring 19 to complete a circuit from one side of battery 37, terminal 39, wire 41, retainer disk 28, collector grid 17, surface of collector ring 19, terminal 36, preamplifier circuit 40, electronic circuit 38 to the other side of battery 37. A small ion transfer current is thus generated and amplified in preamplifier circuit 40. Electronic circuit 38 monitors this current and, if its level becomes large enough, an alarm is sounded indicating the presence of product ions of interest, and thus the chemical agent in the gas of interest G is detected.

Figure 2:
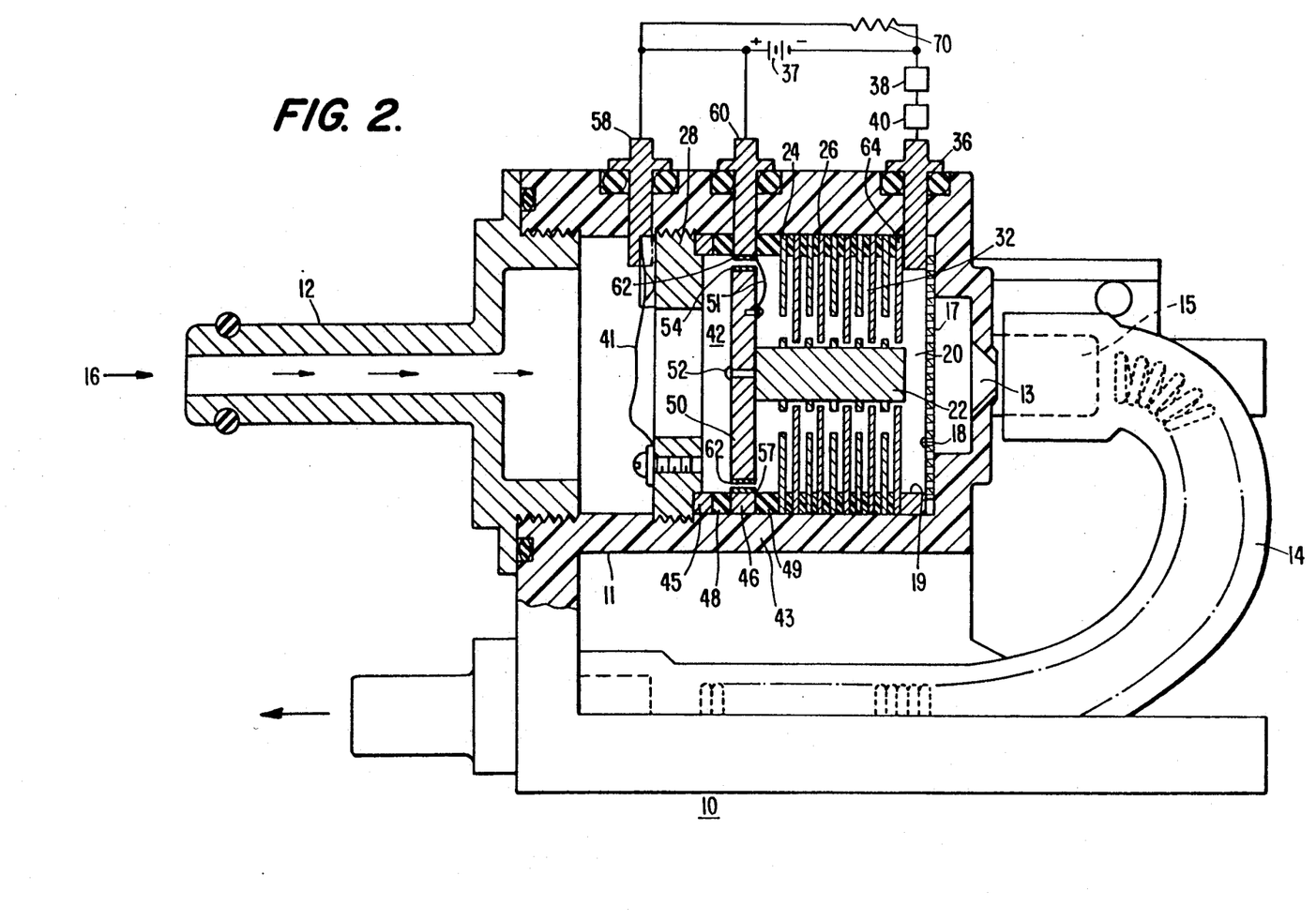
FIG. 2 is a cross-sectional view illustrating a gas detection apparatus constructed in accordance with a preferred embodiment of the present invention.
Figure 3:
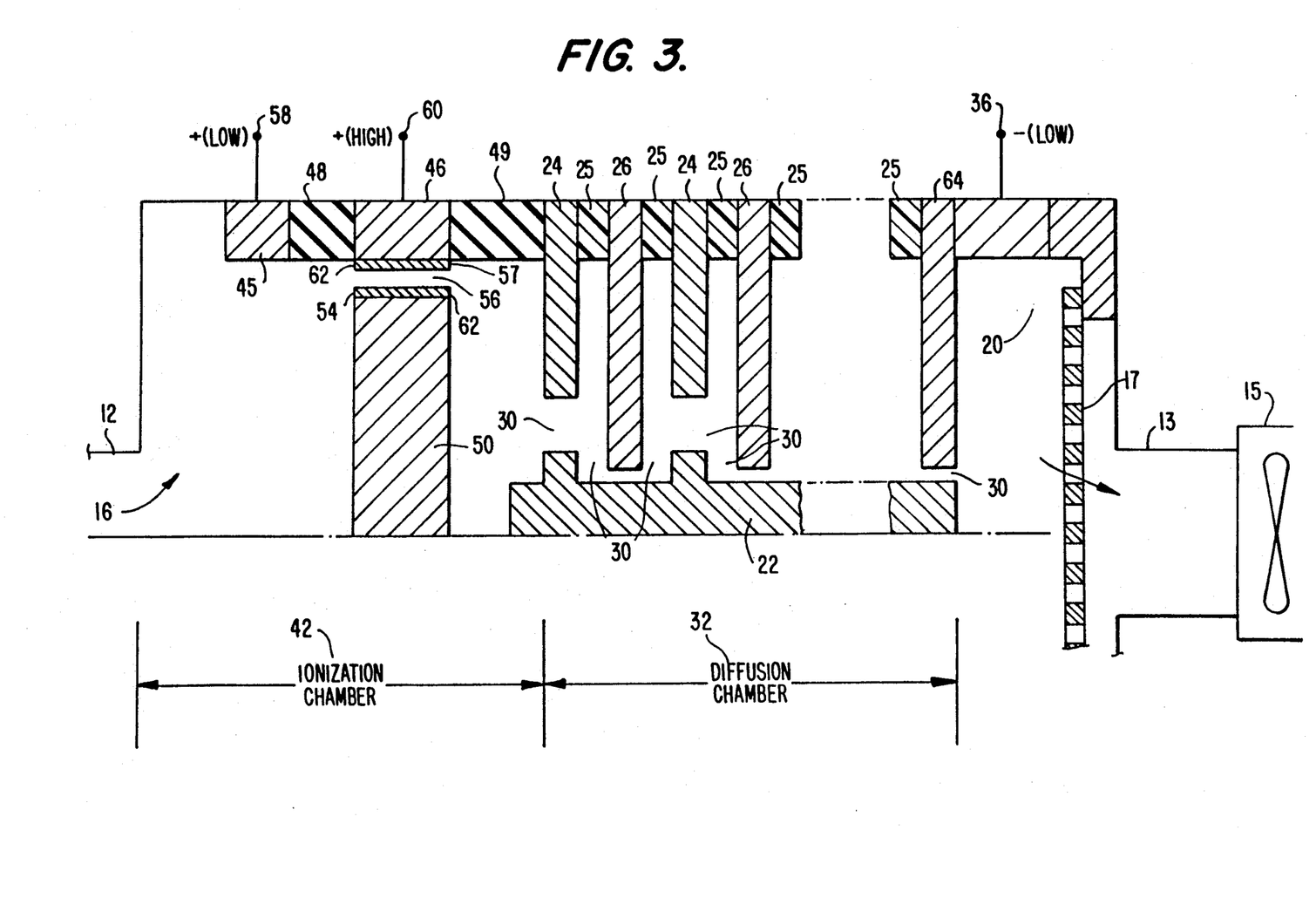
FIG. 3 is a schematic diagram of the gas detection apparatus of the present invention illustrating the radioactive source on the inner and outer periphery of the radiation passage portion of the ionization chamber.

A gas detection apparatus which constitutes a preferred embodiment of the invention is shown in FIGS. 2 and 3 and is represented generally by the numeral 10. Apparatus 10 is preferably built within a chemical agent gas detector unit. Inlet 12 allows the air stream under test, air stream 16, to enter into interior bipolar ionization chamber 42.

In accordance with the invention, the apparatus includes means for conducting an air stream through an ionization chamber, a diffusion chamber, and a collection chamber at a constant rate. As embodied herein, the conducting means consists of air pump 15 which pulls air stream 16 through bipolar ionization chamber 42, diffusion chamber 32 and collection chamber 20, which are in communication with each other in housing 11 of apparatus 10, at such fixed rate. Preferably, air pump 15 is positioned downstream of exhaust pipe 14.

In accordance with the invention, apparatus 10 further includes means mounted in the ionization chamber for generating an electrostatic field for neutralizing ions of a first charge type. The means for generating the electrostatic field is fit into an internally formed peripheral groove 43 in housing 11. As embodied herein, and referring to FIGS. 2 and 3, annular metallic ring 45 which serves as an electrode for connection to a low voltage source, for example, slidably fits in housing 11.

Annular metallic ring 46, which may be of a configuration similar to annular metallic ring 45, is coaxially mounted in ionization chamber 42 but spaced from annular metallic ring 45. Ring 46 may be connected to a high voltage source, for example. Annular ring 48, made of insulating material, is positioned between annular metallic rings 45 and 46 to provide necessary electrical insulation.

Annular metallic ring 46 is positioned adjacent to annular ring 48. Ring 46 is insulatively and physically separated from baffle plates 24 in diffusion chamber 32 by annular ring 49 which is made of a suitable insulating material. A disk-shaped metallic member 50, which is preferably connected to voltage source 37 through wire 51, annular metallic ring 46 and terminal 60, thereby having the same potential as annular metallic ring 46, is mounted in ionization chamber 42 concentric to annular metallic ring 46 and may be conventionally connected to manifold 22 by screw 52. Metallic disk 50 has a diameter such that its peripheral surface 54 forms an annular radiation passage 56 with internal peripheral surface 57 of annular metallic ring 46.

In describing the present embodiment of the invention in connection with FIG. 2 and FIG. 3, it is assumed that ring 45 which serves as an electrode is connected to an external low voltage source through terminal 58 and that ring 46 and disk 50, which also serve as electrodes, are connected to a higher voltage source through terminal 60.

A potential of from 0 to 11 volts is provided on electrode ring 45 and a potential of from 11 to 20 volts is provided on electrode ring 46 and electrode disk 50. Electrostatic field 66 (FIG. 4) is created by the difference in potential between electrode ring 45 and electrode ring 46 and electrode disk 50. Negatively-charged electrostatic field 66 is created when the voltages of the above-mentioned polarities and values are applied.

Figure 5:
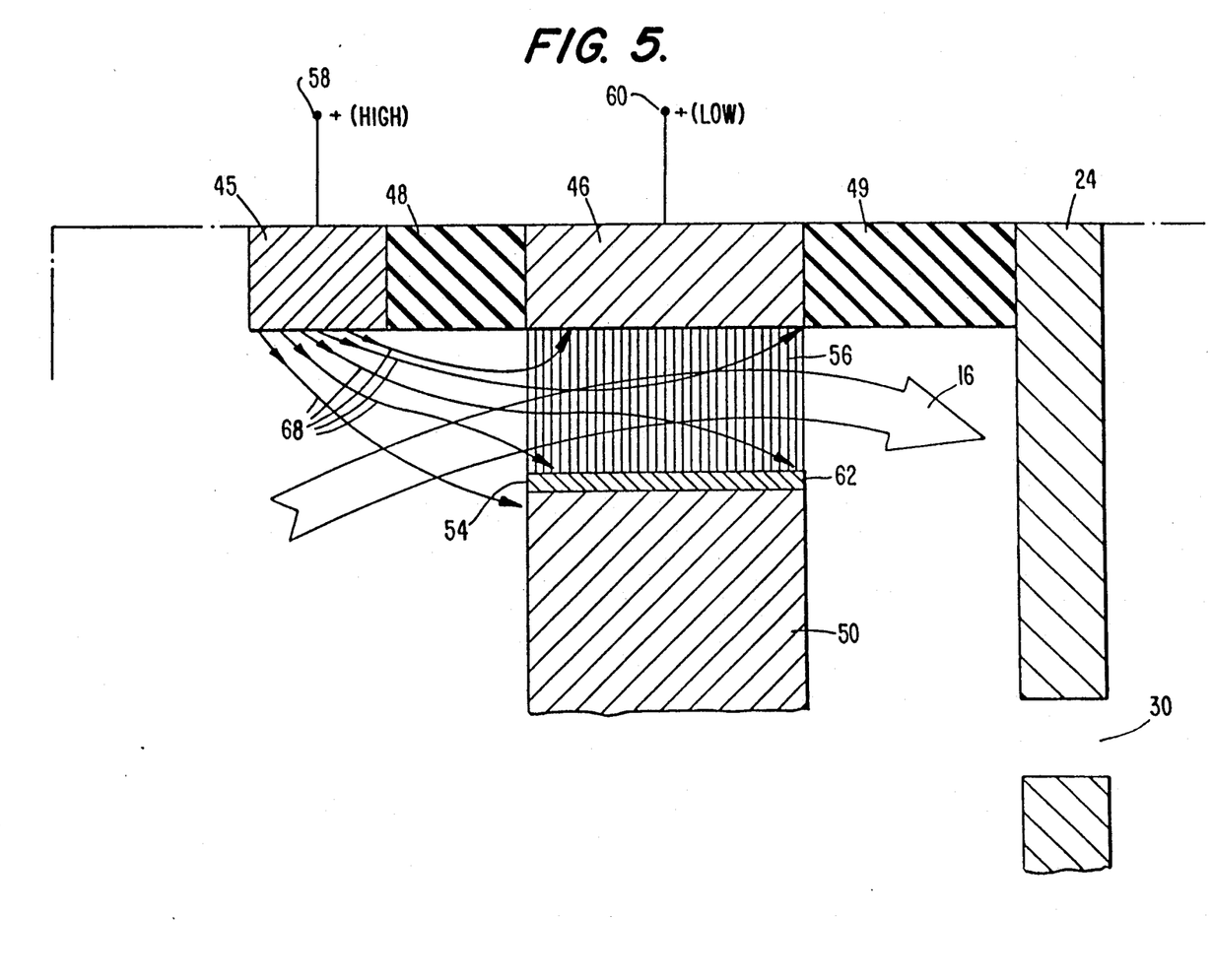
FIG. 5 is a schematic diagram illustrating the interaction of a positively-charged electrostatic field with an air stream including ion clusters.

It is preferable to create an electrostatic field on the order of 10-15 volts/cm for a cell module with a flow path length of 3 cm in order to detect chemical agents in the air sample with a volume flow rate of 1.3 liters per minute. The magnitude of the electrostatic field may be controlled by controlling the externally-applied potentials, the space between the electrodes, and the exposed surface area of the electrodes. The values of the voltages applied to electrode ring 45, electrode ring 46 and electrode disk 50 can be reversed in order to create a positively-charged electrostatic field, such as shown in FIG. 5. It should be noted that arrangements other than two metallic ring-shaped electrodes 45 and 46 and single disk-shaped electrode 50 could be employed to create this electrostatic field without departing from the spirit or scope of the invention.

In accordance with the invention, radiation means are mounted in the ionization chamber for generating reactant and product ions of first and second charge types. As embodied herein, the mounting of the radiation means is within radiation passage 56. The radioactive source 62 is preferably Nickel 63 material, which will enable a reduction of the potential radiation hazard by a ratio of 1000 to 1 from the current source material in use, Americium 241. Other such low-level radioactive materials can be employed, however, apart from Nickel 63, within the spirit and scope of the invention.

Preferably, radioactive source 62 is electro-deposited on peripheral surface 54 of electrode disk 50. However, radioactive source 62 may also be electro-deposited on surfaces 54 and 57 of electrode disk 50 and electrode ring 46, respectively, as shown in FIG. 3. Alternatively, radioactive source 62 could be placed on a surface independent of either of electrode disk 50 or electrode ring 46. In known fashion, radioactive source 62 ionizes air stream 16 by releasing radioactive particles which collide with the air molecules and Causes reactant ions and product ions to be formed within air stream 16.

In accordance with the present invention, the apparatus further includes baffle means mounted in the diffusion chamber for conducting the ionized air stream through a labyrinthine path for neutralizing reactant ions of the second charge type. As embodied herein, an assembly of disk-shaped baffle plates 24 and 26, coaxially spaced by annular Teflon spacers 25, are attached to manifold 22, and these plates, spacers and manifold slidably fit into housing 11 to form the diffusion chamber. Baffle plates 24 and 26 have openings or flow orifices 30 therein to form a labyrinthine path in diffusion chamber 32, the same as done in the prior art showing of FIG. 1. At the end of diffusion chamber 32 is a metal spacer 64 defining a last flow orifice 30 adjacent manifold 22.

Collection chamber 20 is placed downstream of diffusion chamber 32 and adjacent gold spacer 64. Collection chamber 20 has a collector grid 17 at the end thereof. Collector grid 17 is mounted adjacent to and covers outlet 13. Collector grid 17 is preferably retained in position in housing 11 by a metallic collector ring 19. Collection chamber 20 is connected to a terminal 36 through which a low electrical potential is applied. In collection chamber 20, the velocity of ionized air stream 16 is reduced to allow collision of the remaining ions with the inner peripheral surface of collector ring 19 and with the surface of grid 17 in collection chamber 20. Such collisions cause a subsequent charge transfer thereby to complete a circuit from one side of battery 37, resistor 72, terminal 58, wire 41, retainer disk 28, electrode 45, electrode 50, collector grid 17, surface of collector ring 19, terminal 36, preamplifier circuit 40, electronic circuit 38 to the other side of battery 37.

The entire assembly comprised of members 17, 19, 22, 24, 26, 45, 46, 48, 49 and 50 is slidably mounted in housing 11 and positioned by annular retainer 28 which is threaded in housing 11 to maintain such members in physical engagement with each other in housing 11.

The operation of the apparatus constructed according to the present invention will now be described in connection with FIGS. 3 and 4 and assuming air stream 16 includes a chemical agent of interest. Air stream 16 enters apparatus 10 through inlet 12. Air pump 15 pulls the air through apparatus 10 at a fixed rate. As air stream 16 flows past radioactive source 62, radioactive source 62 ionizes air stream 16 by releasing radioactive particles which collide with the air molecules and causes ion clusters of reactant ions and product ions to be formed within air stream 16.

Figure 4:
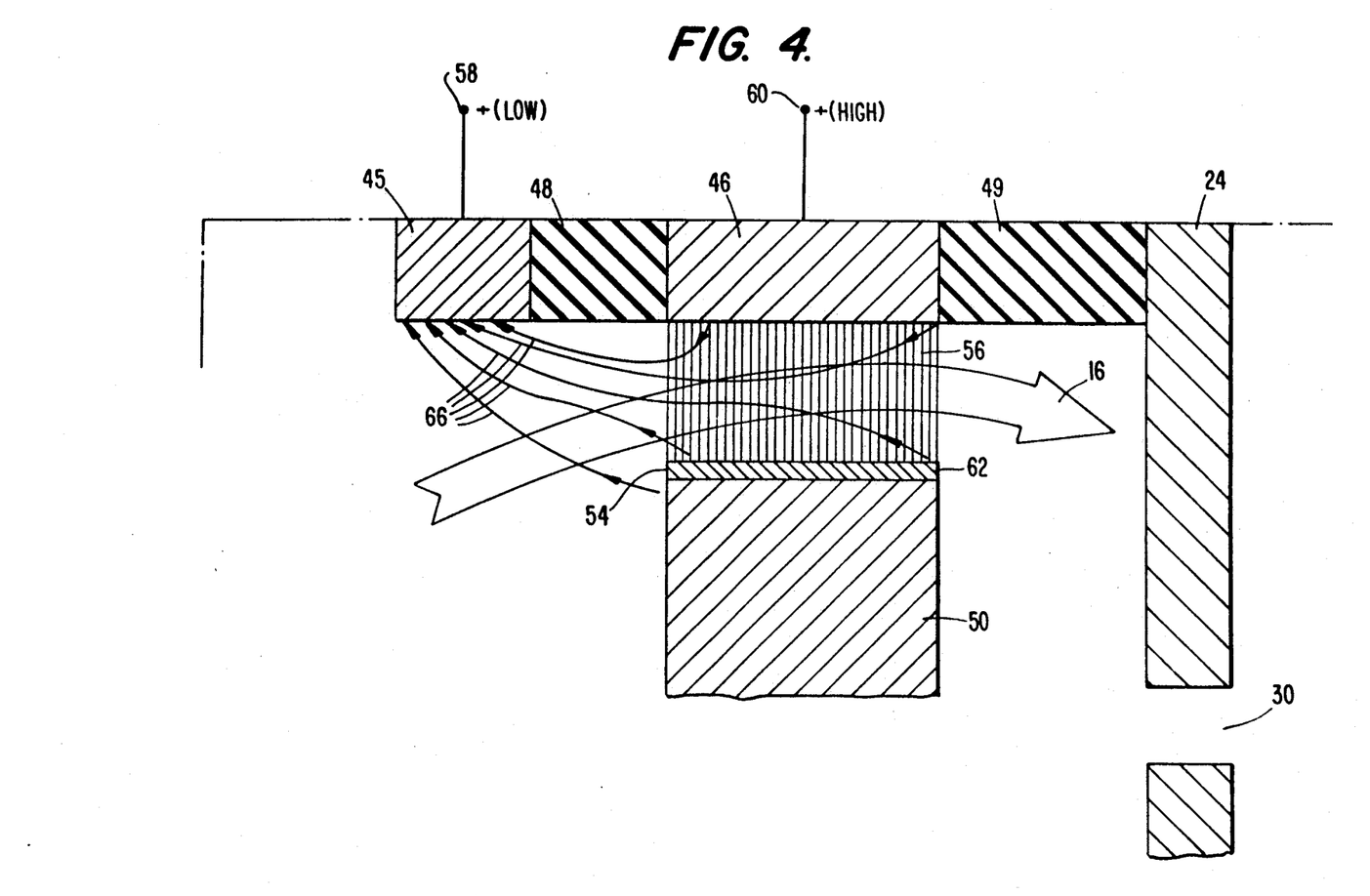
FIG. 4 is a schematic diagram illustrating the interaction of a negatively-charged electrostatic field with an air stream including ion clusters.

A negatively-charged electrostatic field 66 is shown in FIG. 4. This charge type is created by applying a low potential to electrode ring 45 and a high potential to electrode ring 46 and electrode disk 50. Electrostatic field 66 produces forces which act on positively-charged ions in the direction of the arrows on the electrostatic field 66 force lines. The velocity of the positively-charged ions is retarded in the flow direction. The negatively-charged ions, when subjected to electrostatic field 66, increase speed in the direction of flow and collide with the exposed surfaces of electrode ring 46 and electrode disk 50. These collisions result in a charge transfer whereby the negatively-charged ions are neutralized and returned to air stream 16. The surface charge on electrode ring 46 and electrode disk 50 is restored by the externally-applied voltage potentials. This process produces an abundance of positively-charged ions when compared to the quantity of negatively-charged ions remaining following neutralization. The abundance of positively-charged ions is used to react with the agent gas to form product ions.

With reference to FIG. 5, a positively-charged electrostatic field 68 can be created by reversing the values of the voltages applied to electrode ring 45 and 46 and electrode disk 50. This configuration is used in order to enhance the abundance of negatively-charged ions when detecting a chemical agent which forms negative ions, for example. The velocity of the negatively-charged ions is retarded in the flow direction and the positively-charged ions increase speed in the direction of flow and collide with the exposed surfaces of electrode ring 46 and electrode disk 50 and are thereby neutralized.

After being subjected to the electrostatic field, air stream 16 is then directed through diffusion chamber 32 in which the known ion selection process takes place. The reactant ions with ion mobilities greater than 2.0 $cm^2v^{-1}s^{-1}$ become neutralized either by collision with the surface area of the baffles or by recombination with ions of opposite polarity in the flow of the air stream. Therefore, mainly those ions of ion mobilities less than 2.0 $cm^2v^{-1}s^{-1}$—the product ions sought to be detected—will complete the passage through diffusion chamber 32.

The product ions completing the passage through diffusion chamber 32 are then detected as a result of the reduction in the velocity of the air flow causing the product ions to collide with collector ring 19 and grid 17 and to transfer their charge. When a low electrical potential is created in collection chamber 20, a small ion transfer current is generated and amplified in preamplifier circuit 40. A electronic circuit 38 monitors this current and, if it becomes large enough, as, for example, by exceeding a preset level or threshhold, an alarm is sounded. Collection chamber 20 and corresponding electronic circuits suitable for such purposes are well known in the art and need not be described in further detail for purposes of understanding the present invention.

As can be appreciated from the foregoing, the introduction of an electrostatic field, here created by the use of electrode rings 45 and 46 and electrode disk 50, into apparatus 10 acts to minimize the recombination of the positive and negative reactant ions. This increases the efficiency of the overall gas detection apparatus 10. The neutralized ions will not interfere with the formation of product ions of the polarity type sought to be detected and, thus, more of the product ions of the type sought to be detected will ultimately reach collection chamber 20 and can induce a greater current. This allows a radioactive source with a lower radioactive strength to be used since less radioactive source strength is needed in order to form a detectable number of product ions. The apparatus is also more sensitive because it can detect a lesser quantity of chemical agent in an air stream. The invention benefits the user of a gas detection apparatus by lowering the potential radiation hazard to the user. By using controlled electric field forces and flow forces to limit the production of ions in the ionization chamber to ions of a single polarity, the invention provides a method for converting bipolar ionization chambers to monopolar ionization chambers while allowing the use of a low energy radioactive source. It should be noted that the principle of the invention can be applied to detect any type of large molecular compound and is not limited to detection of chemical agent molecules.

It will be apparent to those skilled in the art that various modifications and variations can be made to the gas detection apparatus of the present invention without departing from the scope or spirit of the invention. Thus, it is intended that the present invention cover the modifications and variations of the invention, provided they come within the scope of the appended claims and their equivalents.

What is claimed is:

1. A gas detection apparatus, comprising:
   a housing including an ionization chamber, a diffusion chamber, and a collection chamber in flow communication with each other;
   means for conducting an air stream through said chambers at a constant rate along a flowpath;
   radiation means including a radioactive material mounted in said ionization chamber for generating reactant ions of first and second respective charge types and product ions of said first and second respective charge types;
   means for generating an electrostatic field for increasing the velocity of the reactant ions of said first charge type while decreasing the velocity of reactant ions of said second charge type, said means including a plurality of axially spaced electrically conductive members for connection to respective different voltage potentials mounted in said ionization chamber, said radioactive material being disposed on a surface of at least one of said plurality of axially spaced members;
   baffle means mounted in said diffusion chamber for causing said air stream from the ionization chamber to follow a labyrinthine path for neutralizing ions having a mobility greater than a predetermined amount; and
   circuit means responsive to the presence of product ions of said second charge type in said collection chamber for completing an electrical circuit.

2. The gas detection apparatus as recited in claim 1, wherein said radiation material is comprised of Nickel 63.

3. The gas detection apparatus as recited in claim 1, wherein said electrostatic field generating means includes:
   a first annular metallic member mounted in said ionization chamber and having an inner peripheral surface extending in the direction of the flowpath;
   a second annular metallic member mounted in said ionization chamber, said second member having an inner peripheral surface extending in the direction of the flowpath and coaxially spaced from said first member;
   a disk-shaped metallic member mounted in said ionization chamber and having a peripheral surface extending in the direction of the flowpath and concentrically spaced from said inner peripheral surface of said second member to form an annular axially extending passage defining the flowpath therebetween;
   means for connecting said first member to a first voltage source; and
   means for connecting said second member and said disk-shaped member to a second voltage source having a potential different from said first voltage source.

4. The gas detection apparatus as recited in claim 3, wherein said radioactive material has a radiation level substantially less than Americium 241 and is disposed on said peripheral surface of said disk-shaped member.

5. The gas detection apparatus as recited in claim 3, wherein said radioactive material has a radiation level substantially less than Americium 241 and is disposed on said inner peripheral surface of said second member and on said peripheral surface of said disk-shaped member.

6. A gas detection apparatus, comprising:
   a housing including an ionization chamber, a diffusion chamber, and a collection chamber in communication with each other;
   means for conducting an air stream through said chambers at a constant rate;
   radiation means including a radioactive material mounted in said ionization chamber for generating reactant and product ions of first and second respective charge types, said radiation material being comprised of Nickel 63;
   means mounted in said ionization chamber for generating an electrostatic field for increasing the velocity of the reactant ions of said first charge type while decreasing the velocity of recantations of the second charge type, said electrostatic field generating means including
      a first annular metallic member having an inner peripheral surface mounted in said ionization chamber,
      a second annular metallic member mounted in said ionization chamber, said second member having an inner peripheral surface coaxially spaced from said first member,
      a disk-shaped metallic member mounted in said ionization chamber and having a peripheral surface concentrically spaced from said inner peripheral surface of said second member to form a passage therebetween having the radioactive material disposed on at least one of the peripheral surfaces of said second member and said disk-shaped metallic member, said reactant ions of said first charge type of increased velocity colliding with said second annular member and said disk-shaped metallic member, thereby to provide an abundance of reactant ions of said second charge type for reacting with the gas to form product ions of said second charge type,
      means for connecting said first member to first voltage source, and
      means for connecting said second member and said disk-shaped member to a second voltage source having a potential different from said first voltage source;
   baffle means mounted in said diffusion chamber for causing said ionized air stream to follow a labyrinthine path for neutralizing reactant ions of said second charge type; and
   circuit means responsive to the presence of said product ions of said second charge type in said collection chamber for completing an electrical circuit.

7. A method of gas detection, comprising:
   conducting an air stream from an inlet end through an ionization, diffusion, and collecting chamber to an outlet end at a substantially constant rate;

ionizing radioactively the air stream at an electrically conductive surface coated with a radioactive material having a radiation level substantially less than Americium 241 for forming reactant ions of first and second charge types and product ions of the first and second charge types in the ionization chamber;

subjecting the air stream in the ionization chamber to an electrostatic field having a selected potential applied to said coated surface and a potential difference in the direction of air stream flow for increasing the velocity of the reactant ions of the first charge type and decreasing the velocity of the reactant ions of the second charge type;

neutralizing the reactant ions of the first charge type and thereby increasing the ratio of the reactant ions of the second charge type to the reactant ions of the first charge type, for creating an abundance of ions of the second charge type to form product ions of the second charge type;

diffusing the air stream in the diffusion chamber for further neutralizing remaining ions in the air stream having a mobility greater than a predetermined amount and conducting to the collection chamber ions in the air stream having a mobility no greater than said predetermined amount, and completing an electric circuit in response to the presence of product ions of the second charge type in the collecting chamber.

8. The gas detection apparatus of claim 1 wherein the means for generating an electrostatic field for increasing the velocity of the reactant ions, includes a surface disposed to be impacted by the reactant ions of increased velocity.

* * * * *

UNITED STATES PATENT AND TRADEMARK OFFICE
CERTIFICATE OF CORRECTION

PATENT NO. : 5,114,677
DATED : May 19, 1992
INVENTOR(S) : Michael F. Steele et al.

It is certified that error appears in the above-identified patent and that said Letters Patent is hereby corrected as shown below:

Claim 6, column 10, line 28, "recantations" should read --reactant ions--;

Claim 7, column 12, line 11, "collecting" should read --collection--.

Signed and Sealed this

Twenty-eighth Day of September, 1993

Attest:

BRUCE LEHMAN

*Attesting Officer*    Commissioner of Patents and Trademarks